(12) United States Patent
Roh et al.

(10) Patent No.: US 9,405,714 B2
(45) Date of Patent: Aug. 2, 2016

(54) METHOD AND APPARATUS FOR MANAGING SENSOR DATA AND METHOD AND APPARATUS FOR ANALYZING SENSOR DATA

(75) Inventors: Yohan J Roh, Yongin-si (KR); Seok-jin Hong, Hwaseong-si (KR); Sang-dok Mo, Hwaseong-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 450 days.

(21) Appl. No.: 13/295,785

(22) Filed: Nov. 14, 2011

(65) Prior Publication Data

US 2012/0246261 A1 Sep. 27, 2012

(30) Foreign Application Priority Data

Mar. 22, 2011 (KR) ........................ 10-2011-0025401

(51) Int. Cl.
| | | |
|---|---|---|
| G06F 19/00 | (2011.01) | |
| G06F 13/38 | (2006.01) | |
| H04L 29/06 | (2006.01) | |
| H04L 29/08 | (2006.01) | |
| H04L 12/26 | (2006.01) | |
| A61B 5/00 | (2006.01) | |

(52) U.S. Cl.
CPC .......... *G06F 13/385* (2013.01); *H04L 43/0817* (2013.01); *H04L 65/1053* (2013.01); *H04L 65/1083* (2013.01); *H04L 67/36* (2013.01); *A61B 5/0022* (2013.01); *G06F 19/3418* (2013.01); *G06F 2213/3808* (2013.01)

(58) Field of Classification Search
None
See application file for complete search history.

(56) References Cited

U.S. PATENT DOCUMENTS

| | | | | |
|---|---|---|---|---|
| 6,239,707 B1* | 5/2001 | Park | ............................... | 340/576 |
| 6,584,376 B1* | 6/2003 | Van Kommer | ....... | G05D 1/0285 |
| | | | | 379/88.03 |
| 7,429,914 B2* | 9/2008 | Carlson | ..................... | G01S 5/06 |
| | | | | 340/286.01 |
| 7,471,995 B1* | 12/2008 | Robinson | .......................... | 701/3 |
| 8,217,828 B2* | 7/2012 | Kirk | ................................ | 342/62 |
| 2001/0014914 A1* | 8/2001 | Muramatsu et al. | .......... | 709/224 |
| 2002/0148477 A1* | 10/2002 | Kwoen | ................ | A61B 5/0002 |
| | | | | 340/573.1 |
| 2003/0100983 A1* | 5/2003 | Bullinger | .............. | B60R 21/013 |
| | | | | 701/45 |
| 2003/0220821 A1* | 11/2003 | Walter et al. | ..................... | 705/3 |

(Continued)

FOREIGN PATENT DOCUMENTS

| | | |
|---|---|---|
| KR | 1997-0013822 | 3/1997 |
| KR | 10-2008-0041911 A | 5/2008 |
| KR | 10-2009-0049757 A | 5/2009 |

OTHER PUBLICATIONS

Wei, Mingzhu, et al. "Supporting a spectrum of out-of-order event processing technologies: from aggressive to conservative methodologies." Proceedings of the 2009 ACM SIGMOD International Conference on Management of data. ACM (2009): 1031-1033.

(Continued)

*Primary Examiner* — Ninos Donabed
(74) *Attorney, Agent, or Firm* — NSIP Law

(57) ABSTRACT

Provided are an apparatus and method for transmitting only sensor data actually used to process a user request among sensor data received from a sensor when communication restarts between a sensor data management device and a sensor data analysis device. Accordingly, the amount of data transmitted to the sensor data analysis device is reduced. The sensor data analysis device may analyze the sensor data received from the sensor data management device to process the user request.

14 Claims, 7 Drawing Sheets

(56) References Cited

U.S. PATENT DOCUMENTS

| | | | | |
|---|---|---|---|---|
| 2004/0139385 A1* | 7/2004 | Sakaue | G06F 1/3203 | 715/210 |
| 2004/0158376 A1* | 8/2004 | Knueppel | B60R 21/013 | 701/45 |
| 2005/0130671 A1* | 6/2005 | Frank | G01S 5/0252 | 455/456.1 |
| 2005/0208969 A1* | 9/2005 | Kwoen | A61B 5/0002 | 455/557 |
| 2005/0222933 A1* | 10/2005 | Wesby | G06Q 40/00 | 705/36 R |
| 2005/0256956 A1* | 11/2005 | Littlefield | G06Q 10/06 | 709/225 |
| 2005/0273219 A1* | 12/2005 | Kitao | B60R 25/00 | 701/2 |
| 2006/0207941 A1* | 9/2006 | Morikawa | G01N 30/88 | 210/656 |
| 2007/0168332 A1* | 7/2007 | Bussard | H04L 12/1818 | |
| 2007/0266117 A1* | 11/2007 | Pomies | H04L 29/06 | 709/218 |
| 2008/0016095 A1* | 1/2008 | Bhatnagar | G06F 17/30306 | |
| 2008/0123605 A1* | 5/2008 | Cho | H04W 48/04 | 370/338 |
| 2008/0176713 A1* | 7/2008 | Olivera Brizzio | A63B 24/00 | 482/8 |
| 2008/0319666 A1* | 12/2008 | Petrov | G01C 21/005 | 701/469 |
| 2009/0042518 A1* | 2/2009 | Ido | B60R 25/2018 | 455/90.2 |
| 2009/0055465 A1* | 2/2009 | DePue et al. | | 709/202 |
| 2009/0112853 A1* | 4/2009 | Nishizawa | G06F 17/3053 | |
| 2009/0150560 A1 | 6/2009 | Bestgen et al. | | |
| 2009/0177145 A1* | 7/2009 | Ohlander et al. | | 604/66 |
| 2009/0300525 A1* | 12/2009 | Jolliff | H04M 1/72544 | 715/764 |
| 2010/0049006 A1* | 2/2010 | Magar | A61B 5/0024 | 600/301 |
| 2010/0238801 A1* | 9/2010 | Smith et al. | | 370/229 |
| 2010/0328143 A1* | 12/2010 | Kirk | | 342/26 B |
| 2013/0300578 A1* | 11/2013 | Uchida | | 340/870.02 |

OTHER PUBLICATIONS

Krishnamurthy, Sailesh, et al. "Continuous analytics over discontinuous streams." Proceedings of the 2010 ACM SIGMOD International Conference on Management of data. ACM (2010) (12 pages in English).

* cited by examiner

METHOD AND APPARATUS FOR MANAGING SENSOR DATA AND METHOD AND APPARATUS FOR ANALYZING SENSOR DATA

CROSS-REFERENCE TO RELATED APPLICATION(S)

This application claims the benefit under 35 U.S.C. §119(a) of Korean Patent Application No. 10-2011-0025401, filed on Mar. 22, 2011, in the Korean Intellectual Property Office, the entire disclosure of which is incorporated herein by reference for all purposes.

BACKGROUND

1. Field

The following description relates to methods and apparatuses for receiving, managing, and analyzing sensor data from a sensor.

2. Description of the Related Art

The development of a ubiquitous society has caused an increase in monitoring applications in various fields. The ubiquitous environment creates the feeling that the society has access everywhere or in several places at the same time. Typically a ubiquitous environment is an environment capable of accessing a computing device anytime and anywhere. This is accompanied by the development of communication technology and the development of storing and computing devices. Accordingly, a user may simultaneously receive and transmit information in various fields through the user's mobile device, personal computer (PC), and/or the like.

The information that the user receives may be transmitted from a high performance computing device such as a server or a sensor platform that has a sensor. A communication state between the device of the user and the sensor platform may not be continuous but may be intermittent. Thus, sensor data sensed by the sensor but not transmitted to the mobile device because of temporary disconnection of communication with the mobile device may wait in the sensor platform until the communication restarts. In this example, the more time the communication disconnection takes, the amount of data to be transmitted increases proportionally. As the communication restarts after the disconnection, the amount of data to be transmitted may be significantly greater than that when the communication continues. This may cause a problem in both the sensor platform and the mobile device because a sharp increase in the amount of data to be transmitted may generate a sudden load which may cause rapid battery consumption and malfunction, thereby resulting in inconvenience to the user.

SUMMARY

In one general aspect, there is provided a method of managing sensor data generated by at least one sensor, the method including receiving sensor data from the at least one sensor, checking a communication connection state between a first device for performing the method of managing sensor data and a second device for analyzing the sensor data, and transmitting some of the received sensor data to the second device based on a user's query information for the sensor data and based on the checked communication connection state.

The method may further comprise selecting some of the received sensor data based on the query information, in response to the checked communication connection state indicating communication has restarted from disconnection, wherein the transmitting comprises transmitting the selected sensor data to the second device.

The query information may comprise a query definition in which a user request for the sensor data is defined, and the selecting may comprise extracting sensor data used to process the user request.

The query information may further comprise an allowable delay limit indicating the maximum allowable amount of time that may elapse from a point in time that the sensor data is generated to a time defined by the user, and the selecting may comprise extracting sensor data used to process the user request based on whether a time elapsed from a generation time of the received sensor data to the time defined by the user is within the allowable delay limit.

In response to the query definition indicating a continuous query by which a single query corresponding to the user request is continuously repeated, the selecting may comprise generating a plurality of query windows where each query window is a basic unit of a set of sensor data that is used to process each query in the continuous query, calculating a time elapsed from a generation time of the last sensor data of each query window to the time defined by the user, and extracting sensor data contained in at least one query window of which the calculated elapsed time is less than the allowable delay limit.

The transmitting may comprise transmitting the selected sensor data according to a data transmission policy defining which sensor data is first transmitted among the selected sensor data.

The data transmission policy may indicate a First-In First-Out (FIFO) policy by which the selected sensor data is sequentially transmitted from first generated sensor data.

In response to the query information comprising a continuous query by which a single query corresponding to the user request is continuously repeated, the data transmission policy may indicate a policy of transmitting the selected sensor data in a query window that is length of time that is less than a value that is obtained by subtracting a time elapsed from a generation time of the last sensor data in the query window to the time defined by the user for the allowable delay limit.

The method may further comprise storing the received sensor data based on a data storage policy defining which sensor data among the received sensor data is stored in the first device, wherein the selecting comprises selecting sensor data stored in the first device based on the data storage policy.

The data storage policy may define sensor data to be stored in the first device among the received sensor data based on at least one condition selected from the group consisting of a value of each sensor data, a generation time of each sensor data, the number of pieces of sensor data, and the query information.

In another aspect, there is provided an apparatus for managing sensor data generated by at least one sensor, the apparatus including a device interface for receiving sensor data from the at least one sensor, a communication connection determiner for checking a communication connection state between the sensor data managing apparatus and an apparatus for analyzing the sensor data, a selector for selecting some of the received sensor data based on a user's query information for the sensor data and based on the checked communication connection state, and a network interface for transmitting the selected sensor data to the sensor data analyzing apparatus.

In another aspect, there is provided a computer-readable storage medium having stored therein program instructions to cause a processor to implement method of managing sensor data generated by at least one sensor, the method including receiving sensor data from the at least one sensor, checking a communication connection state between a first device for performing the method of managing sensor data and a second device for analyzing the sensor data, and transmitting some of the received sensor data to the second device based on a user's query information for the sensor data and based on the checked communication connection state.

In another aspect, there is provided a method of analyzing sensor data generated by at least one sensor, the method including receiving a user's query information for the sensor data, transmitting the query information to an apparatus that provides the sensor data, receiving sensor data selected based on the query information from among sensor data generated by the at least one sensor, in response to the transmission of the query information, and analyzing the received sensor data.

The query information may comprise a query definition in which a user request for the sensor data is defined, and the receiving may comprise receiving sensor data that is used to process the user request.

The query information may further comprise an allowable delay limit indicating the maximum allowable amount of time that may elapse from a point in time at which the sensor data is generated by the user, and the receiving may comprise receiving sensor data that is used to process the user request based on whether the time elapsed from the generation time of the received sensor data to the time defined by the user is within the allowable delay limit.

In response to the query definition indicating a continuous query by which a single query corresponding to the user request is continuously repeated, the receiving may comprise generating a plurality of query windows where each query window is a basic unit of a set of sensor data that is used to process each query in the continuous query, calculating a time elapsed from a generation time of the last sensor data of each query window to the time defined by the user, and receiving sensor data contained in at least one query window of which the calculated elapsed time is less than the allowable delay limit.

In another aspect, there is provided an apparatus for analyzing sensor data generated by at least one sensor, the apparatus including a user interface for receiving a user's query information for the sensor data, a network interface for transmitting the query information to an apparatus providing the sensor data and receiving sensor data selected based on the query information from among sensor data generated by the at least one sensor, in response to the transmission of the query information, and a query processor for analyzing the received sensor data.

In another aspect, there is provided a computer-readable storage medium having stored therein program instructions to cause a processor to implement method of analyzing sensor data generated by at least one sensor, the method including receiving a user's query information for the sensor data, transmitting the query information to an apparatus that provides the sensor data, receiving sensor data selected based on the query information from among sensor data generated by the at least one sensor, in response to the transmission of the query information, and analyzing the received sensor data.

In another aspect, there is provided a sensor data managing apparatus including a storage configured to store sensor data obtained by at least one sensor, a determiner configured to determine when communication stops and when communication restarts between the sensor data managing apparatus and a sensor data analyzing apparatus, a selector configured to, in response to the determiner determining communication has restarted, select only a portion of sensor data stored in the storage that was obtained by the at least one sensor while communication was stopped and to exclude a portion of sensor data stored in the storage that was obtained by the at least one sensor while communication was stopped, and an interface to transmit the selected sensor data to the data analyzing apparatus.

The selector may select the portion of sensor data stored in the storage that was obtained by the at least one sensor while communication was stopped based on a user query.

The user query may define at least one of a minimum age of sensor data and a minimum size of sensor data.

Other features and aspects may be apparent from the following detailed description, the drawings, and the claims.

Figure 1:
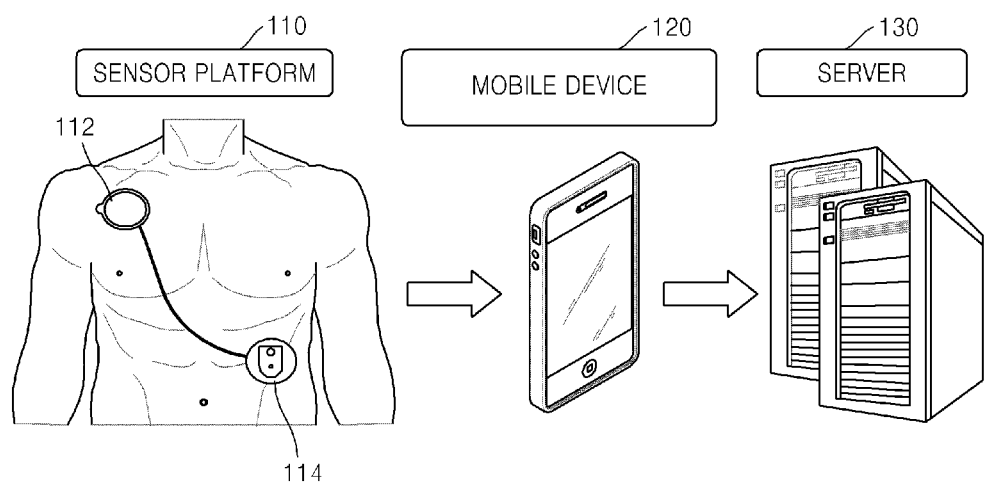
FIG. 1 is a diagram illustrating an example of a relationship between a sensor platform and a sensor data analyzing apparatus including a mobile device and a server.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following detailed description is provided to assist the reader in gaining a comprehensive understanding of the methods, apparatuses, and/or systems described herein. Accordingly, various changes, modifications, and equivalents of the methods, apparatuses, and/or systems described herein will be suggested to those of ordinary skill in the art. Also, descriptions of well-known functions and constructions may be omitted for increased clarity and conciseness.

Various examples herein relate to a sensor data managing method and a sensor data managing apparatus. In the following description, functions or constructions well-known to those of ordinary skill in the field may be omitted.

The development to a ubiquitous society may spread the use of monitoring applications in various fields, such as traffic, finance, the environment, and the like. Thus, although various examples are described for fields such as healthcare, the following description is not limited thereto.

FIG. 1 illustrates an example of a relationship between a sensor platform and a sensor data analyzing apparatus including a mobile device and a server.

Referring to FIG. 1, a relationship diagram may be considered as an example in the healthcare field. The relationship diagram is divided into a sensor platform 110 and a sensor data analyzing apparatus. The sensor platform 110 includes a sensor 112 and a sensor data managing apparatus 114. The sensor data analyzing apparatus indicates all devices for receiving sensor data from a sensor platform and processing a user request based on the sensor data. In this example, the sensor data analyzing apparatus includes a mobile device 120 that may perform real-time processing and analysis of sensor data and that may act as a gateway and a high-performance computing device. In some examples, the sensor data analyzing apparatus may include a server 130 for receiving data from the mobile device 120 or directly from the sensor platform 110 and analyzing the data. In various examples, the mobile device 120 may be used to analyze the sensor data.

The sensor 112 may be attached to a human body to generate sensor data that may be communicated and computed from various signals, such as a body temperature and a heart rate that are capable of being sensed from the human body. The sensor 112 may transmit the generated sensor data to the sensor data managing apparatus 114. The sensor data managing apparatus 114 may wirelessly transmit the sensor data to the server 130 through the mobile device 120 that acts as a gateway. A low-power near field communication technique such as BLUETOOTH®, ZIGBEE®, and the like, may be used to transmit the sensor data between the sensor platform 110 and the mobile device 120 acting as a gateway.

The mobile device 120 may use various communication techniques to perform communication with the server 130, for example, long-distance communication. As another example, the sensor data managing apparatus 114 may directly transmit the sensor data to the server 130 without passing through a gateway such as the mobile device 120.

Figure 2:
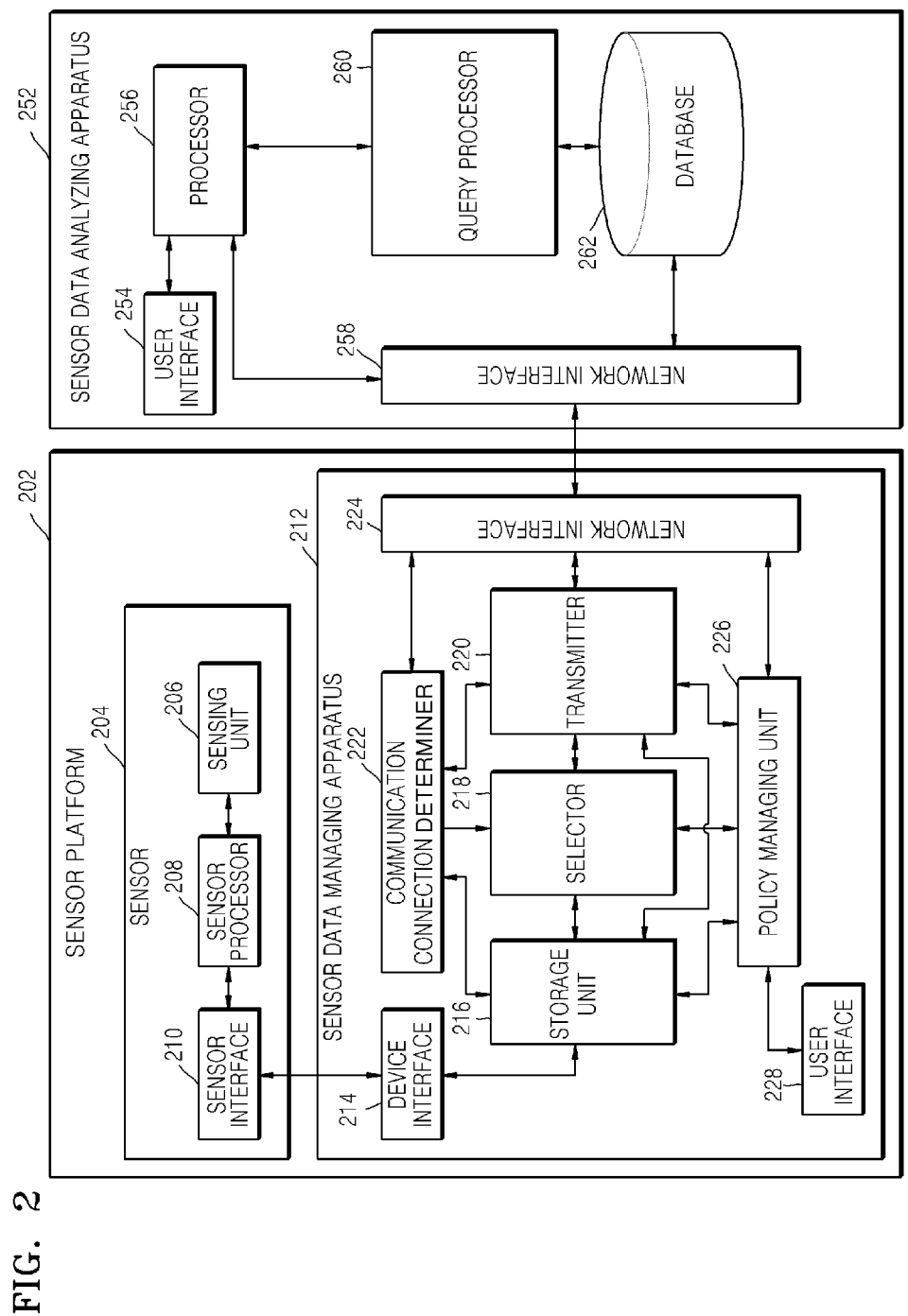
FIG. 2 is a diagram illustrating an example of a sensor platform that includes a sensor data managing apparatus and a sensor, and a sensor data analyzing apparatus.

FIG. 2 illustrates an example of a sensor platform and a sensor data analyzing apparatus.

Referring to FIG. 2, sensor platform 202 includes a sensor 204 and a sensor data managing apparatus 212. FIG. 2 also includes a sensor data analyzing apparatus 252 for receiving sensor data from the sensor platform 202 and analyzing the sensor data. The sensor platform 202 and the sensor data analyzing apparatus 252 form a sensor system.

The sensor platform 202 includes the sensor 204 and the sensor data managing apparatus 212. The sensor 204 may include various types of sensors used in various fields. For example, the sensor 204 may sense signals such as light, heat, pressure, vibration, electrical signals, biosignals, and the like. The sensor data managing apparatus 212 may receive sensor data from the sensor 204 and manage the sensor data before transmitting the sensor data to the sensor data analyzing apparatus 252. For example, the sensor 204 and the sensor data managing apparatus 212 may be physically connected or may be separated, and a connection between the sensor 204 and the sensor data managing apparatus 212 may be achieved via a wired or wireless scheme.

The sensor 204 includes a sensing unit 206, a sensor processor 208, and a sensor interface 210. The sensing unit 206 may receive various stimuli from the outside, and a form of the sensing unit 206 may vary based on the type of signal sensed from the outside. For example, if an external signal received by the sensing unit 206 relates to temperature, the sensing unit 206 may sense the temperature, and if the external signal relates to light, the sensing unit 206 may sense the light. The sensor processor 208 may generate data from the signal sensed by the sensing unit 206 to perform communication and computation. That is, a stimulus or signal from the outside is not transmitted or computed as is. For example, the sensor processor 208 may generate quantitative sensor data to represent the signal. The sensor interface 210 is a communication interface that is used to transmit the sensor data generated by the sensor 204 to the sensor data managing apparatus 212. The sensor interface 210 is connected to a device interface 214 of the sensor data managing apparatus 212. The interfaces may be in a wired or wireless form.

The sensor data managing apparatus 212 includes the device interface 214, a storage unit 216, a selector 218, a transmitter 220, a communication connection determiner 222, a network interface 224, a policy management unit 226, and a user interface 228.

The device interface 214 of the sensor data managing apparatus 212 is connected to the sensor interface 210 of the sensor 204 to receive the sensor data generated by the sensor 204 via a wired or wireless connection.

The storage unit 216 may store the sensor data. For example, the storage unit 216 may include a database for storing the sensor data. The storage unit 216 is connected to the communication connection determiner 222. If the communication connection determiner 222 determines that communication is disconnected, the storage unit 216 may store sensor data according to a storage policy by confirming the storage policy from the policy management unit 226. The storage policy may define sensor data to be stored based on at least one condition selected from the group consisting of a condition based on a sensor data value, a condition based on a time such as a time elapsed from when sensor data is generated or when communication is disconnected, a condition based on a sensor data amount, and a condition based on whether sensor data relates to a user's query. For example, suppose there are 10 pieces of data 1 to 10, and this 10-piece data set is called first data. If there is a storage policy for storing only data having a value equal to or less than 5, second data having 5 pieces of data such as 1 to 5 of the first data, may be newly defined. Thus, the storage policy may be used to store only data suitable for use in the sensor data analyzing apparatus 252, resulting in a decrease in an amount of data amount to be transmitted to the sensor data analyzing apparatus 252.

The selector 218 may check query information from the policy management unit 226 and select sensor data according to the query information, in response to the communication connection determiner 222 determining that communication has restarted. This is different from the storage unit 216 that may store only sensor data suitable for use in the sensor data analyzing apparatus 252. For example, while the storage unit 216 may store only sensor data matching a data range or condition suitable for use in the sensor data analyzing apparatus 252, the selector 218 may select sensor data to be used for the sensor data analyzing apparatus 252 to process a user request. In various examples, the selector may exclude some of the sensor data, for example, data that overlaps, and may select only some of the data to be transmitted to the data analyzing apparatus 252.

That is, while the selector 218 may select sensor data to be actually used to process a user request, the storage unit 216 may store only data in a form or range suitable for use in the sensor data analyzing apparatus 252 regardless of whether the stored data is actually used for information analysis in the sensor data analyzing apparatus 252. Sensor data to be used for the sensor data analyzing apparatus 252 to process a user request may vary according to query information.

The query information may include the definition of a query to define the user request and an allowable delay limit. As described in various examples, the delay limit refers to the maximum allowable amount of time that may elapse from a point in time at which the sensor data is generated to a time defined by the user as a selection criterion on whether sensor data is used to process the user request. In various examples, a type or contents of the query may vary according to the definition of the query, and a selection method may vary according to the type or contents of the query. Also, a value of the allowable delay limit may vary according to settings by the user.

Because only sensor data to be actually used to process the user request is selected by the selector 218, a sensor data amount may be reduced, resulting in a decrease in a sensor data amount to be transmitted. Although the selection of sensor data is performed after a communication restart in the current example, it should be appreciated that the selection may be performed before the communication restart.

The transmitter 220 may transmit the selected sensor data to the sensor data analyzing apparatus 252 based on a transmission policy from the policy management unit 226. The transmission policy indicates a method of transmitting the selected sensor data to the sensor data analyzing apparatus 252 in a form capable of being used by the sensor data analyzing apparatus 252. For example, the method may be a method of sequentially transmitting the selected sensor data from the first generated data or a method of transmitting the sensor data from sensor data in a window that has a shorter existence time than others. In this latter example, the existence time may be a time obtained by subtracting an age of a window (definitions of a window and an age of the window will be described later) from the allowable delay limit.

The communication connection determiner 222 may determine a communication connection state between the sensor platform 202, the sensor data managing apparatus 212, and the sensor data analyzing apparatus 252. The determination result may be checked by the storage unit 216, the selector 218, and the transmitter 220.

The network interface 224 may be used by the sensor data managing apparatus 212 to communicate with the sensor data analyzing apparatus 252. For example, the network interface 224 may be a network card. The network interface 224 of the sensor data managing apparatus 212 may be connected to a network interface 258 of the sensor data analyzing apparatus 252 and may be used to transmit selected data or receive data such as a storage policy, query information, or a transmission policy, from the sensor data analyzing apparatus 252. The network interface 224 may support low-power near field communication techniques, such as BLUETOOTH® and ZIGBEE®. The sensor platform 202 may communicate with a mobile device acting as a gateway to transmit sensor data to a high-performance computing device, such as a server, that is located far away from the sensor platform 202, by using low-power near field communication techniques. If a distance between the sensor platform 202 and the mobile device is farther than a distance that is supported by such a low-power near field communication technique, communication between the sensor platform 202 and the mobile device may be disconnected.

The policy management unit 226 may have the storage policy that is used by the storage unit 216, the query information used by the selector 218, and the transmission policy used by the transmitter 220 so that the storage unit 216, the selector 218, and the transmitter 220 may use the storage policy, the query information, and the transmission policy, respectively. The policy management unit 226 may include a database for managing the policies and the query information. The policies may be transmitted from the sensor data analyzing apparatus 252 based on input of a user through a user interface 254 of the sensor data analyzing apparatus 252 or input through the user interface 228 of the sensor data managing apparatus 212 of the sensor platform 202.

The user interface 228 may be used by the user to directly input information about the storage policy, the query information, and/or the transmission policy to the sensor data managing apparatus 212. For example, the storage policy, the query information, and the transmission policy may be input through the user interface 254 of the sensor data analyzing apparatus 252 or directly input by the user through the user interface 228 of the sensor data managing apparatus 212.

The sensor data analyzing apparatus 252 includes the user interface 254, a processor 256, the network interface 258, a query processor 260, and a database 262.

The user interface 254 may be used by users to input a storage policy, query information, and/or a transmission policy to be used by the storage unit 216, the selector 218, and the transmitter 220, respectively, as described above.

The processor 256 may process the information received from the user interface 254 and transmit and receive information to and from the network interface 258 and the query processor 260.

The network interface 258 may perform communication by being connected to the network interface 224 of the sensor data managing apparatus 212 as described above.

The query processor 260 may process a query of a user and may use sensor data stored in the database 262. For example, the query processor 260 may establish a query implementation plan, optimize the query implementation plan, and process the query according to the query implementation plan.

The database 262 may store sensor data received from the sensor data managing apparatus 212.

Figure 3:
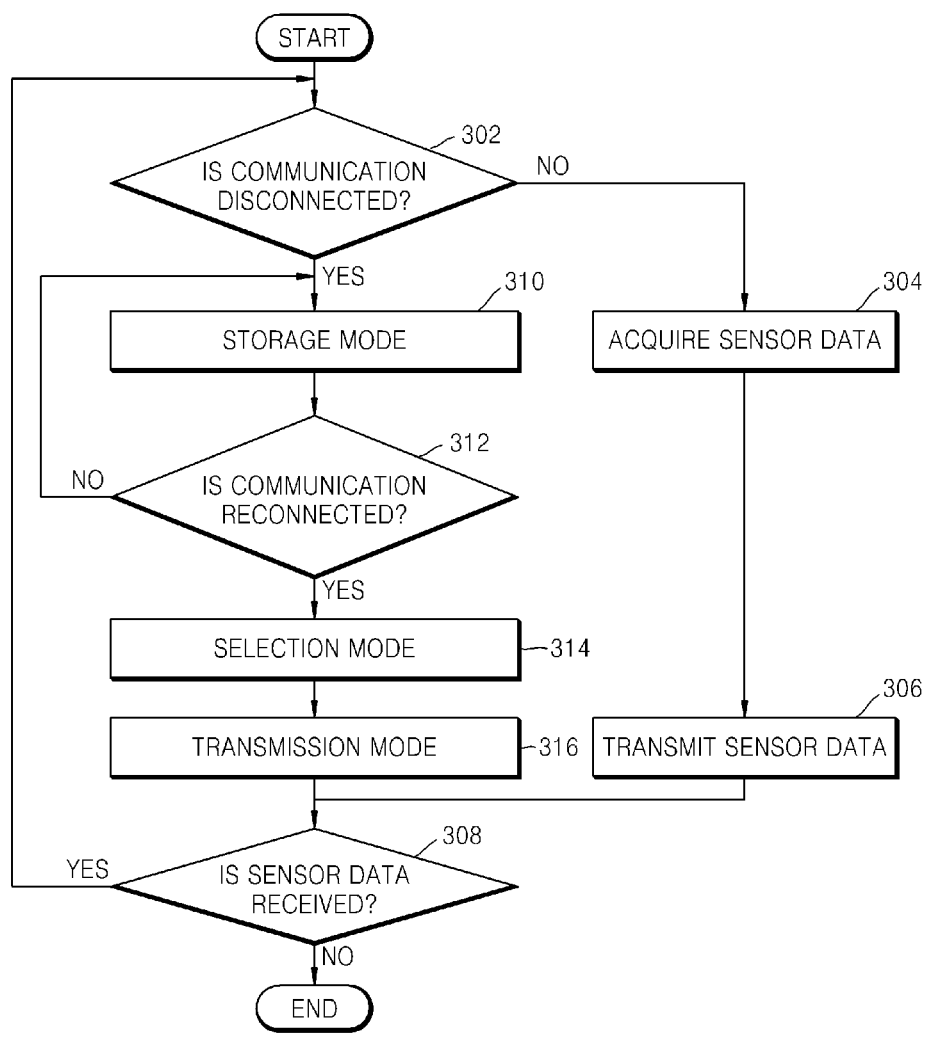
FIG. 3 is a flowchart illustrating an example of a sensor data managing method.

FIG. 3 illustrates an example of a sensor data managing method. The example of FIG. 3 is a method of managing sensor data according to a communication connection state between the sensor platform 202, including the sensor data managing apparatus 212, and the sensor data analyzing apparatus 252.

The sensor data managing method begins in response to the sensor data managing apparatus 212 receiving sensor data from the sensor 204.

In 302, the sensor data managing apparatus 212 checks a state of a communication connection with the sensor data analyzing apparatus 252. The communication connection state between the sensor platform 202 and the sensor data analyzing apparatus 252 may be an intermittent state in which communication is not continuous and is instead repeatedly disconnected and connected. Examples of reasons for disconnection include when a power source is turned off because of full discharge of a battery in the sensor data analyzing apparatus 252 or when a distance between the sensor platform 202 and the sensor data analyzing apparatus 252, such as a mobile device, is too far to communicate with each other through a low-power near field communication technique. Based on these considerations, the sensor data managing apparatus 212 may use a different method of managing sensor data received from the sensor 204 by determining whether communication has stopped due to a communication disconnection state between the sensor data managing apparatus 212 and the sensor data analyzing apparatus 252 or communication is performed due to a communication connection state therebetween.

If the apparatus 212 detects that communication between the sensor data managing apparatus 212 and the sensor data analyzing apparatus 252 is connected in 302, the sensor data managing apparatus 212 acquires sensor data received from the sensor 204 through the network interface 224, in 304, and transmits the sensor data to the sensor data analyzing apparatus 252, in 306. If it is determined that there is no more sensor data to be received, in 308, the sensor data managing apparatus 212 ends the method until sensor data is newly received from the sensor 204. As another example, if there is more sensor data to be received in 308, the sensor data managing apparatus 212 proceeds to 302 again to receive the sensor data.

Otherwise, if communication between the sensor data managing apparatus 212 and the sensor data analyzing apparatus 252 is disconnected, in 302, the sensor data managing apparatus 212 performs a storage mode in which sensor data received from the sensor 204 is stored as a new type of sensor data according to a storage policy, in 310. An example of the storage mode is shown in the flowchart of FIG. 4.

Figure 4:
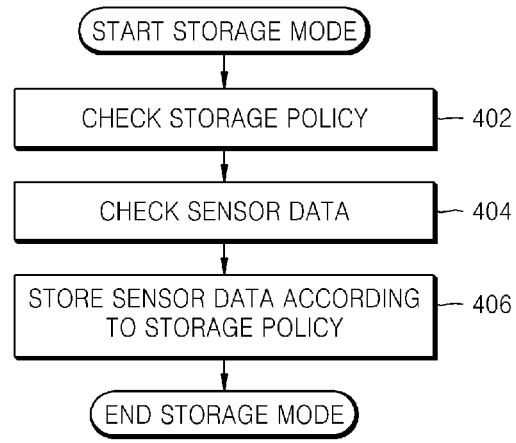
FIG. 4 is a flowchart illustrating an example of a storage mode corresponding to operation 310 of FIG. 3.

FIG. 4 illustrates an example of the storage mode corresponding to operation 310 of FIG. 3.

In 402, the sensor data managing apparatus 212 checks a storage policy to determine whether sensor data is suitable for use in the sensor data analyzing apparatus 252. As described above, the storage policy may be used to define sensor data to be stored based on at least one selected condition from the group consisting of a condition based on a sensor data value, a condition based on a time, such as a time elapsed from when sensor data is generated or when communication is disconnected, a condition based on a sensor data amount, and a condition based on whether sensor data relates to a user's query.

In an example of the sensor platform 202 in the healthcare field, if the sensor 204 measures a body temperature of a human being every minute, the measured sensor data values may be temperature data values of about 36.5° C., which is the average body temperature. In this example, if a body temperature lower than 25° C. or higher than 50° C. is considered death, the condition based on a sensor data value may be a condition that body temperature data satisfies a value equal to or higher than 25° C. and equal to or lower than 50° C. The condition based on a time may be a condition that body temperature data satisfies a value within 60 minutes before a communication re-connection time in a case in which communication disconnection continues for 180 minutes by assuming that very old body temperature data is not suitable as a sensor data value, with reference to the example previously mentioned. Because the sensor 204 measures a body temperature of a human being every minute, to acquire 10 pieces of body temperature data, body temperature data within 10 minutes may be acquired by using the condition based on time. However, 10 pieces of lately measured body temperature data may also be acquired as adequate body temperature data by counting the number of pieces of body temperature data under the condition based on a sensor data amount. In a case of the condition based on whether sensor data relates to a user's query, if the contents of the query are to obtain a mean value of measured body temperatures, all of measured body temperature data satisfies this condition as sensor data related to the query. The above-described conditions may be combined and used. For example, only body temperature data satisfying both the condition that body temperature data satisfies a value equal to or higher than 25° C. and equal to or lower than 50° C. and the condition that body temperature data satisfies a value within 30 minutes before a communication reconnection time may be stored as new sensor data.

In 404, the sensor data managing apparatus 212 checks sensor data to which the storage policy is applied. Sensor data received from the sensor 204 may be the sensor data to which the storage policy is applied.

In 406, the sensor data managing apparatus 212 may store only sensor data satisfying a condition corresponding to the storage policy by checking that the sensor data received from the sensor 204 satisfies the condition.

Referring again to FIG. 3, in 312, the sensor data managing apparatus 212 checks whether communication with the sensor data analyzing apparatus 252 has been reconnected. If communication with the sensor data analyzing apparatus 252 has not been reconnected, the sensor data managing apparatus 212 proceeds back to the storage mode in 310. Otherwise, if communication with the sensor data analyzing apparatus 252 has been reconnected, the sensor data managing apparatus 212 proceeds to a selection mode, in 314. Examples of the selection mode are described with reference to FIGS. 5 to 7. Although a process of selecting sensor data is performed after the communication restarts in the current embodiment, the selection process may be performed before the communication restarts.

Figure 5:
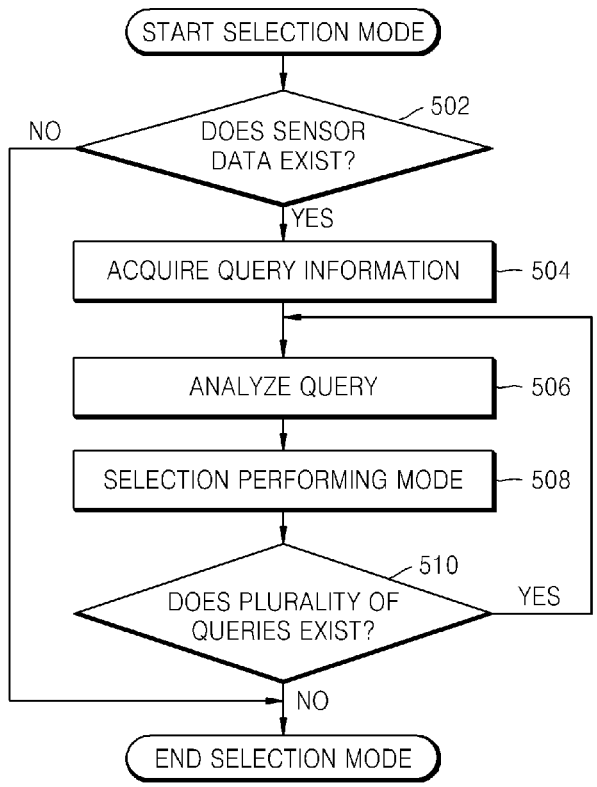
FIG. 5 is a flowchart illustrating an example of a selection mode corresponding to operation 314 of FIG. 3.

FIG. 5 illustrates an example of the selection mode corresponding to operation 314 of FIG. 3.

In 502, the sensor data managing apparatus 212 checks whether sensor data exists in the storage unit 216. The storage unit 216 may have sensor data received from the sensor 204 or sensor data conforming to the storage policy. For example, no sensor data may exist in the storage unit 216 because no sensor data conforming to the storage policy may exist while performing the storage mode of 310. If no sensor data exists in the storage unit 216, there is no sensor data to be selected. Accordingly, the selection mode ends. Otherwise, if sensor data exists, the sensor data managing apparatus 212 proceeds to operation 504.

In 504, the sensor data managing apparatus 212 acquires and confirms query information, which is a criterion of the selection. The query information may include the definition of a query that is used to define a user requirement and an allowable delay limit.

In 506, the sensor data managing apparatus 212 analyzes the type and contents of a query from the definition of a query. This is performed because a selection performing mode of 508 varies based on the type and contents of a query. That is, the selection performing mode may be performed to be suitable for the type and contents of a query by analyzing the type and contents of a query. Hereinafter, for ease of understanding, a selection process performed in the selection performing mode is described in the case of a continuous query by which a single query corresponding to a user request is continuously repeated at each predetermined interval. It should be appreciated however that the selection performing mode according to the current example is not limited thereto.

In 508, the sensor data managing apparatus 212 performs the selection performing mode in which sensor data is selected. An example of a process and a result based on a continuous query are shown in and described with reference to FIGS. 6 and 7. Also, terms related to the continuous query are described with reference to FIGS. 6 and 7.

Figure 7:
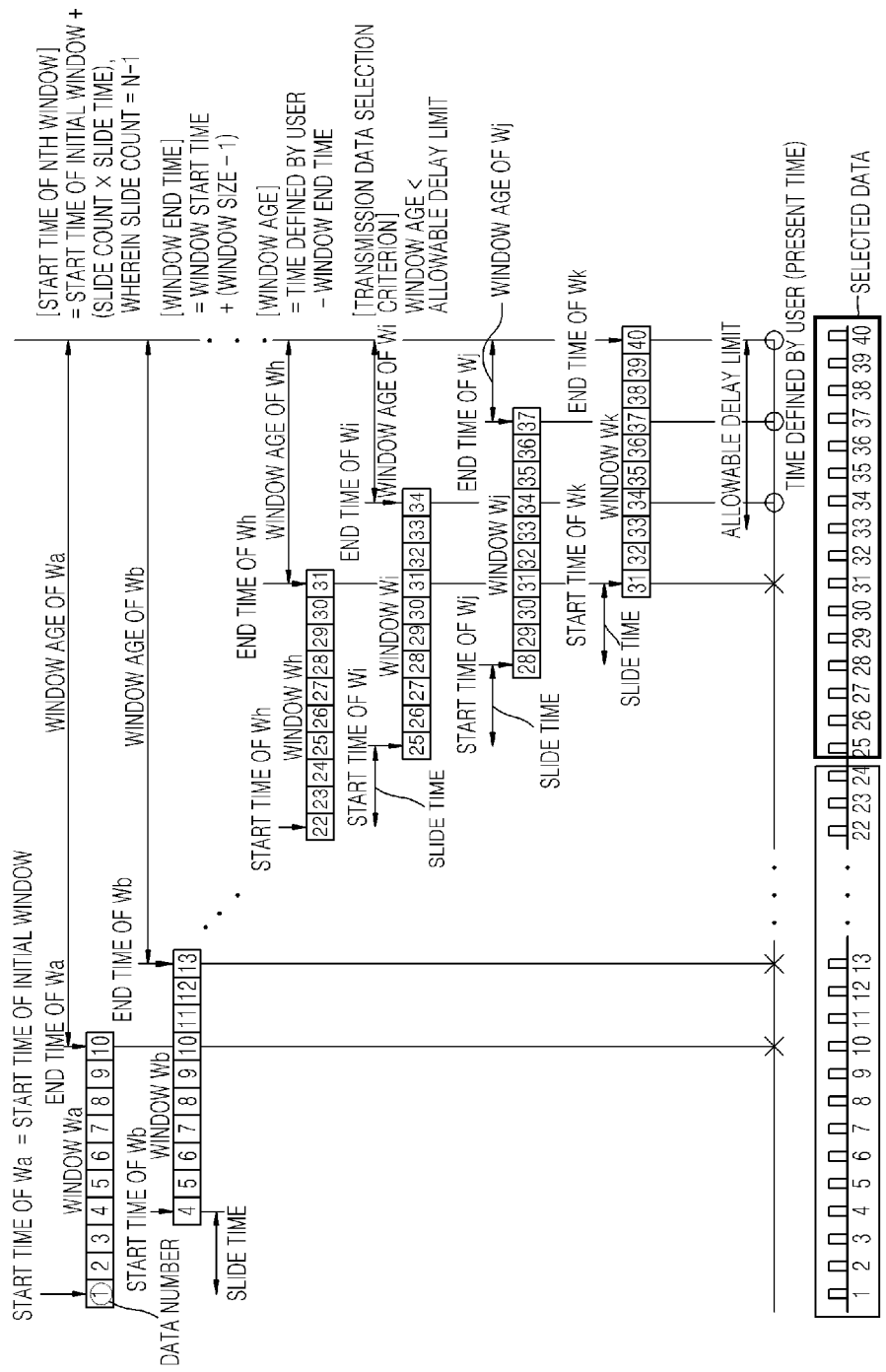
FIG. 7 is a diagram illustrating an example of a data selection process according to the selection performing mode of FIG. 6.

A query indicates a user request as described above, and a query window (hereinafter, window) indicates a basic unit of a sensor data set that is used to process each query in a continuous query. Referring to FIG. 7, 11 windows Wa to Wk are used for a total of 40 pieces of data.

In this example, a single window includes 10 pieces of data indicating a window size. The window size may vary according to the contents of a query. For example, the window size may be defined based on a time, a data amount, a data tuple, and the like.

An initial window indicates a first window for a query in a continuous query. That is, the initial window indicates a window including first generated data. Wa denotes the initial window in FIG. 7.

A window start time indicates a generation time of first generated data in a window. In Wa of FIG. 7, a generation time of the first data is a window start time. In this example, because Wa is an initial window, the generation time of the first data of Wa may be called a start time of the initial window. In Wb, a generation time of the fourth data is the window start time, and in Wk, a generation time of the 31st data is the window start time.

Comparing a start time of an arbitrary window with a start time of a next window, there is a time difference of 3 pieces of data. If every single piece of data is generated at a one-minute interval, the generation of 3 pieces of data indicates a time lapse of 3 minutes, which is referred to as a slide time. Thus, the next window may be obtained by moving the arbitrary window by the slide time. Accordingly, a start time of an Nth window may be obtained using the start time of the initial window and the slide time as shown in Equation 1.

Start time of Nth window=start time of initial window+(slide count×slide time), wherein slide count=N−1  (1)

Referring to FIG. 7, the start time of the initial window Wa is the generation time of the first data, and if it is assumed that the start time of the initial window Wa is 1, a start time of the eleventh window Wk is obtained by 1+((11−1)×3)=31 that is the generation time of the $31^{st}$ data.

A window end time indicates an end time of a single window, i.e., a generation time of last data in the window and may be obtained by Equation 2.

Window end time=window start time+(window size−1)  (2)

Referring to FIG. 7, an end time of the window Wa is obtained by 1+(10−1)=10, which is a generation time of the 10th data.

An age of a window indicates a time that has elapsed from a window end time indicating a generation time of the last sensor data in the window to a time defined by the user, i.e., a time delayed until the time defined by the user because data in the window was not transmitted to the sensor data analyzing apparatus 252 due to disconnection of communication. An age of a window may be obtained by Equation 3.

Window age=time defined by user−window end time  (3).

A window age of the window Wa is obtained with reference to FIG. 7 as an example. In this example, the time defined by the user is a present time denoted by 40. Because a window end time of the window Wa is 10, a window age of the window Wa is 40−10=30. When window ages are sequentially obtained from the window Wb, a window age of the window Wb is 27, a window age of a window We is 24, . . . , a window age of a window Wh is 9, a window age of a window Wi is 6, a window age of a window Wj is 3, and a window age of the window Wk is 0, and the like.

Figure 6:
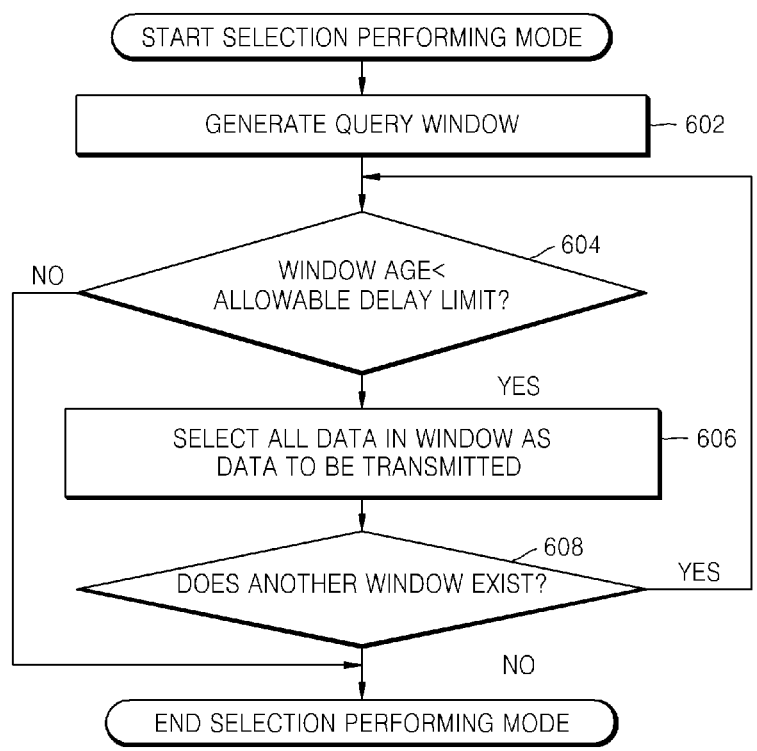
FIG. 6 is a flowchart illustrating an example of a selection performing mode corresponding to operation 508 of FIG. 5.

FIG. 6 illustrates an example of the selection performing mode. In this example, it is assumed that a total of 40 pieces of first to fortieth body temperature data are measured at 1-minute intervals and a user wants mean body temperature information for 10 minutes at every 3-minute interval with the body temperature data. A query is defined to search for and extract data to process the user request. The type of the query is a continuous query, the contents of which may include a time period of 10 minutes (a window size) for limiting a size of a body temperature data set for obtaining a mean value and a time interval of 3 minutes (a slide time). Based on this example, query analysis is performed in 506 of FIG. 5, and the selection performing mode of operation 508 is performed according to an analysis result.

FIG. 6 illustrates an example of the selection performing mode corresponding to operation 508 of FIG. 5.

In 602, each window for a continuous query is generated. This may be performed by searching for the first data and perceiving a window size and a slide time according to the contents of the query. Operation 602 is further described with reference to FIG. 7. Because the first data of FIG. 7 is initial body temperature data and a mean body temperature for 10 minutes is obtained, the number of body temperature data values measured for 10 minutes is 10 if a body temperature measurement cycle is 1 minute. In this example, the body temperature data measured for 10 minutes, i.e., a set of 10 pieces of data, composes a single window. Because a mean value is calculated at every 3-minute interval, a slide time is 3 minutes. Thus, as shown in FIG. 7, the $1^{st}$ data to $10^{th}$ data are included in the initial window Wa, and the fourth data to $13^{th}$ data measured after 3 minutes are included in the second window Wb. Likewise, by considering a slide time of 3 minutes, the 11 windows Wa to Wk are generated as shown in FIG. 7. Some data included in each window may be overlapped according to the slide time if the slide time is less than the window size. In other words, a single piece of data may be included in a plurality of windows. If all windows for the query are generated, all the terms, such as the window start time, the window end time, and the window age, may be perceived.

In 604, a data selection is performed by comparing an age of each window with an allowable delay limit. As described above, the allowable delay limit indicates the maximum allowable amount of a time that may elapse from a point in time at which sensor data is generated to a time defined by the user. If an age of an arbitrary window is less than the allowable delay limit, all data included in the arbitrary window may be selected as data to be transmitted to the sensor data analyzing apparatus 252.

An example of the allowable delay limit is described further described herein. In this example, a user defines the allowable delay limit as 7 minutes from a present time (i.e., when the time defined by the user is the present time) as data to be transmitted and the user desires to obtain mean body temperature information for 10 minutes at every 3-minute interval, the allowable delay limit is 7 minutes. Here, because a single piece of data may be used in a plurality of windows, all data included in at least one window having a window age less than the allowable delay limit is selected as data to be transmitted to the sensor data analyzing apparatus 252.

In 606, if an age of each window is less than the allowable delay limit, all data included in a corresponding window is selected as data to be transmitted to the sensor data analyzing apparatus 252.

After the data selection process for the corresponding window is completed, it is determined in 608 whether any window for which the data selection process has not been performed exists. If any window for which the data selection process has not been performed exists, the sensor data managing apparatus 212 proceeds to operations 604 and 606 for a corresponding window, and if no window for which the data selection process has not been performed exists, the selection performing mode ends.

According to the example of FIG. 7, if operations 602, 604, and 606 are performed for all windows, all body temperature data included in the 3 windows Wi, Wj, and Wk having window ages that are less than the allowable delay limit, 7, is selected as a result. That is, the $25^{th}$ to $34^{th}$ body temperature data included in the window Wi, the $28^{th}$ to $37^{th}$ body temperature data included in the window Wj, and the $31^{st}$ to $40^{th}$ body temperature data included in the window Wk are selected.

In this example, the $28^{th}$ to $37^{th}$ body temperature data are included in two or more windows, however, because they do not have to be transmitted more than once, the number of pieces of body temperature data actually selected to be transmitted to the sensor data analyzing apparatus 252 is 16 corresponding to the $25^{th}$ to $40^{th}$ body temperature data. That is, only 16 pieces of body temperature data are selected from the total of 40 pieces of body temperature data, resulting in an effect of reducing 60% of a transmission amount.

In this example, instead of transmitting ten pieces of body temperature data for each window Wi, Wj, and Wk, or a total of 30 pieces of data, the body temperature data is consolidated, and overlapping data is only transmitted once. As a result of the consolidation, 16 pieces of body temperature data are transmitted instead of 30.

In 510, because a plurality of queries for sensor data may exist, it is determined whether another query exists. If another query exists, the sensor data managing apparatus 212 proceeds to operation 506 to analyze the new query, and if no other queries exist, the selection performing mode ends.

Performing of the selection performing mode for a continuous query has been described with an illustration. In addition to the continuous query, in another example there is a type of a query for searching for an arbitrary data pattern. An example of the performing of the selection performing mode for this case will now be described briefly. A selection is performed by extracting data satisfying a given pattern within a predetermined time range or within a range of a predetermined number of pieces of data.

For example, assuming there is a query of searching for a pattern in which data having a value B appears after data having a value A, data may be sequentially checked from the first data to determine whether it has the value A, and it is checked from when the value A first appears whether the value B appears within the predetermined time range or within the range of a predetermined number of pieces of data. If the value B does not appear within the predetermined time range or within the range of a predetermined number of pieces of data, data immediately next to the data having the value A may be checked to determine whether the data has the value A. If it is found that the data has the value A, a check may be performed from when the value A appears to determine whether the value B appears within the predetermined time range or within the range of a predetermined number of pieces of data. This search process may be repeated.

If the value B appears within the predetermined time range or within the range of a predetermined number of pieces of data, a determination may be made as to whether a time elapsed from a generation time of the value B to the time defined by the user is less than the allowable delay limit. If the elapsed time is less than the allowable delay limit, all data from the data having the value A to the data having the value B may be selected as data to be transmitted. Otherwise, if the elapsed time is equal to or greater than the allowable delay limit, no data may be selected, and data immediately next to the latest data having the value A may be checked to determine whether the data has the value A. If it is found that the data has the value A, whether the value B appears within the predetermined time range or within the range of a predetermined number of pieces of data may be checked. If the value B appears within the predetermined time range or within the range of a predetermined number of pieces of data, it is determined through comparison with the allowable delay limit whether corresponding data is selected. That is, the selection performing mode may be performed according to attributes of a query.

Referring to FIG. 3, in 316, which is described with reference to the flowchart in FIG. 8, the selected data is transmitted to the sensor data analyzing apparatus 252.

Figure 8:
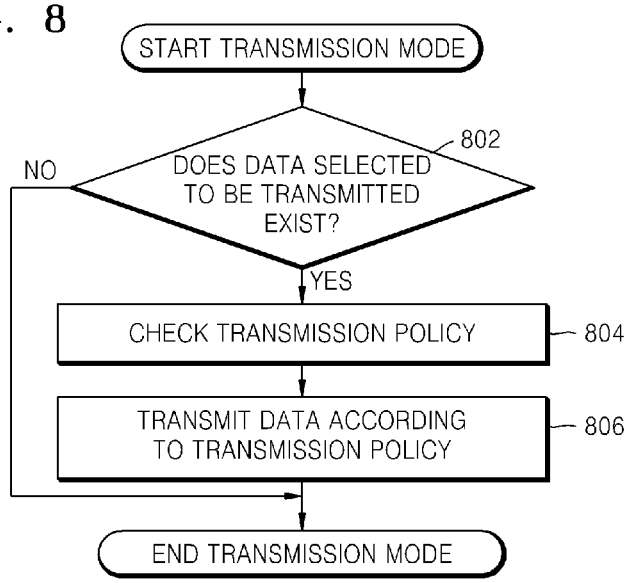
FIG. 8 is a flowchart illustrating an example of a transmission mode corresponding to operation 316 of FIG. 3.

FIG. 8 illustrates an example of a transmission mode corresponding to operation 316 of FIG. 3.

In 802, whether there is sensor data selected as data to be transmitted is determined. If no sensor data to be transmitted exists, there is no data to be transmitted, and the transmission mode ends. If sensor data to be transmitted exists, the sensor data managing apparatus 212 proceeds to 804.

In 804, the sensor data managing apparatus 212 checks a transmission policy by which the selected sensor data is transmitted to the sensor data analyzing apparatus 252 in a form used by the sensor data analyzing apparatus 252. As described above, the transmission policy may be the method of sequentially transmitting the selected sensor data from the first selected one or the method of transmitting the sensor data from sensor data in a window that has a shorter existence time than others.

In 806, the sensor data is transmitted according to the transmission policy. By transmitting all of the sensor data selected according to the transmission policy to the sensor data analyzing apparatus 252, the transmission mode ends. Then, in 308, it is determined whether sensor data has been further received from the sensor 204. If there is no more sensor data to be received, the sensor data managing apparatus 212 ends the process until sensor data is newly received from the sensor 204. Otherwise, if there is more sensor data to be received, the sensor data managing apparatus 212 proceeds to 302 again due to the received sensor data.

Figure 9:
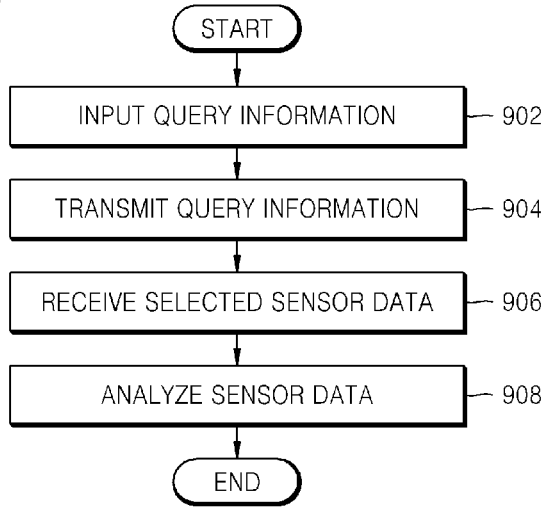
FIG. 9 is a flowchart illustrating an example of a sensor data analyzing method.

FIG. 9 illustrates an example of a sensor data analyzing method. For example, the sensor data analyzing method may be used by the sensor data analyzing apparatus 252 to receive sensor data selected by the sensor data managing apparatus 212.

In 902, the user inputs query information through the user interface 254 of the sensor data analyzing apparatus 252. The user may also input a storage policy and/or a transmission policy.

In 904, the sensor data analyzing apparatus 252 transmits the query information input by the user to the sensor data managing apparatus 212 through the network interface 258. Accordingly, the sensor data managing apparatus 212 selects data to be transmitted as described above. If the storage policy and the transmission policy are also transmitted, data is stored and transmitted using the storage policy and the transmission policy in the storage mode and the transmission mode as described above.

In 906, when sensor data to be transmitted is selected by the sensor data managing apparatus 212 and transmitted to the sensor data analyzing apparatus 252, the sensor data analyzing apparatus 252 receives the sensor data.

In 908, the query processor 260 of the sensor data analyzing apparatus 252 analyzes the sensor data received from the sensor data managing apparatus 212 based on the query information input by the user to process a query of the user.

As described herein in various examples, the amount of sensor data to be transmitted may be reduced by selecting only some sensor data from among sensor data received from a sensor when communication restarts after disconnection, in consideration of the fact that transmission of the sensor data from a sensor platform to a sensor data analyzing apparatus is practically intermittent. Accordingly, a problem of rapidly increasing a load to the sensor platform and the sensor data analyzing apparatus and simultaneously rapidly consuming a battery by transmitting sensor data may be solved.

Program instructions to perform a method described herein, or one or more operations thereof, may be recorded, stored, or fixed in one or more computer-readable storage media. The program instructions may be implemented by a computer. For example, the computer may cause a processor to execute the program instructions. The media may include, alone or in combination with the program instructions, data files, data structures, and the like. Examples of computer-readable storage media include magnetic media, such as hard disks, floppy disks, and magnetic tape; optical media such as CD ROM disks and DVDs; magneto-optical media, such as optical disks; and hardware devices that are specially configured to store and perform program instructions, such as read-only memory (ROM), random access memory (RAM), flash memory, and the like. Examples of program instructions include machine code, such as produced by a compiler, and files containing higher level code that may be executed by the computer using an interpreter. The program instructions, that is, software, may be distributed over network coupled computer systems so that the software is stored and executed in a distributed fashion. For example, the software and data may be stored by one or more computer readable storage mediums. Also, functional programs, codes, and code segments for accomplishing the example embodiments disclosed herein can be easily construed by programmers skilled in the art to which the embodiments pertain based on and using the flow diagrams and block diagrams of the figures and their corresponding descriptions as provided herein. Also, the described unit to perform an operation or a method may be hardware, software, or some combination of hardware and software. For example, the unit may be a software package running on a computer or the computer on which that software is running.

As a non-exhaustive illustration only, a terminal/mobile device described herein may refer to mobile devices such as a cellular phone, a personal digital assistant (PDA), a digital camera, a portable game console, and an MP3 player, a portable/personal multimedia player (PMP), a handheld e-book, a portable lab-top PC, a global positioning system (GPS) navigation, a tablet, a sensor, and devices such as a desktop PC, a high definition television (HDTV), an optical disc player, a setup box, a home appliance, and the like that are capable of wireless communication or network communication consistent with that which is disclosed herein.

A computing system or a computer may include a microprocessor that is electrically connected with a bus, a user interface, and a memory controller. It may further include a flash memory device. The flash memory device may store N-bit data via the memory controller. The N-bit data is processed or will be processed by the microprocessor and N may be 1 or an integer greater than 1. Where the computing system or computer is a mobile apparatus, a battery may be additionally provided to supply operation voltage of the computing system or computer. It will be apparent to those of ordinary skill in the art that the computing system or computer may further include an application chipset, a camera image processor (CIS), a mobile Dynamic Random Access Memory (DRAM), and the like. The memory controller and the flash memory device may constitute a solid state drive/disk (SSD) that uses a non-volatile memory to store data.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A method comprising:
receiving, at a first device, a first piece of sensor data and a second piece of sensor data from a sensor;
storing, in a storage unit included in the first device, the first piece of sensor data and the second piece of sensor data in response to communication being disconnected between the first device and a second device configured to analyze sensor data;
determining that communication has been connected between the first device and the second device;
receiving, at the first device and from the second device, a first query; and
transmitting to the second device, in response to the determination that communication has been connected, the stored first piece of sensor data, but excluding the stored second piece of sensor data, as sensor data selected by the first query,
wherein the first query comprises a continuous query specifying repeated queries, each repeated query requiring pieces of sensor data,
wherein the first query further comprises an allowable delay limit indicating a maximum allowable amount of time that may elapse from a time that sensor data is generated to a predetermined time, and
selecting sensor data selected by the first query comprises:
generating query windows where each query window is a basic unit of a set of sensor data that is used to process each repeated query in the continuous query;
calculating a time elapsed from a generation time of a last sensor data of each query window to the predetermined time; and
extracting sensor data contained in at least one query window of which the calculated elapsed time is less than the allowable delay limit.

2. The method of claim 1, wherein
the receiving from a sensor further includes receiving, while communication is disconnected between the first device and the second device, a third piece of sensor data from the sensor;
the storing comprises determining not to store the third piece of sensor data based on the third piece of sensor data not relating to the first query.

3. The method of claim 1, wherein
the first query comprises a query definition in which a user request for sensor data is defined.

4. The method of claim 1, wherein the transmitting comprises transmitting the selected sensor data according to a data transmission policy defining which sensor data is first transmitted among the sensor data selected by the first query.

5. The method of claim 4, wherein the data transmission policy indicates a First-In First-Out (FIFO) policy by which the sensor data selected by the first query is sequentially transmitted from a first generated sensor data.

6. The method of claim 4, wherein,
in response to the first query comprising a continuous query, the data transmission policy indicates a policy of transmitting the sensor data selected by the first query in a query window,
the continuous query specifying repeated queries, each repeated query requiring a pieces of sensor data, and the query window is a length of time that is less than a value obtained by subtracting a time elapsed from a generation time of a last sensor data in the query window from a predetermined time for an allowable delay limit.

7. The method of claim 1, wherein
the storing comprises selectively storing received pieces of sensor data based on a data storage policy defining which sensor data received at the first device is stored in the storage unit.

8. The method of claim 7, wherein
the data storage policy is based on at least one condition selected from the group consisting of a value of each piece of sensor data, a generation time of each piece of sensor data, a number of pieces of sensor data, and the first query.

9. A sensor data managing apparatus comprising:
an interface device configured to receive sensor data from a sensor;
a network interface processor;
a communication connection determiner processor configured to check a communication connection state for communication between the sensor data managing apparatus and an apparatus for analyzing sensor data via the network interface processor;
a storage unit configured to store a portion of the received sensor data in response to the communication connection determiner processor indicating communication has disconnected; and
a processor configured to:
  receive a first piece of sensor data and a second piece of sensor data via the interface processor,
  store in the storage unit the first piece of sensor data and the second piece of sensor data in response to the communication connection determiner processor indicating communication is disconnected,
  transmit to the apparatus for analyzing sensor data via the network interface processor, in response to the communication connection determiner processor indicating communication with the apparatus for analyzing sensor data has been connected, the stored first piece of sensor data, but excluding the stored second piece of sensor data, as sensor data selected by a first query,
  wherein the first query comprises an allowable delay limit indicating a maximum allowable amount of time that may elapse from a time that the first and second sensor data is generated to a predetermined time, and
  select sensor data through the first query comprising:
    generating query windows where each query window is a basic unit of a set of sensor data that is used to process each repeated query in the continuous query;
    calculating a time elapsed from a generation time of a last sensor data of each query window to the predetermined time; and
    extracting sensor data contained in at least one query window of which the calculated elapsed time is less than the allowable delay limit.

10. A non-transitory computer-readable storage medium having stored therein program instructions to cause a processor to implement a method, the method comprising:
receiving a first piece of sensor data and a second piece of sensor data from a sensor;
storing, in a storage unit connected to the processor, the first piece of sensor data and the second piece of sensor data in response to communication being disconnected between the processor and a second device configured to analyze sensor data;
determining that communication has been connected between the processor and the second device;
receiving from the second device a first query, wherein the first query comprises an allowable delay limit indicating a maximum allowable amount of time that may elapse from a time that the first and second sensor data is generated to a predetermined time; and
transmitting to the second device, in response to the determination that communication has been connected, the stored first piece of sensor data, but excluding the stored second piece of sensor data, as sensor data selected by the first query,
wherein the first query further comprises a continuous query specifying repeated queries, each repeated query requiring pieces of sensor data, and
selecting sensor data selected by the first query comprises:
  generating query windows where each query window is a basic unit of a set of sensor data that is used to process each repeated query in the continuous query;
  calculating a time elapsed from a generation time of a last sensor data of each query window to the predetermined time; and
  extracting sensor data contained in at least one query window of which the calculated elapsed time is less than the allowable delay limit.

11. A method, comprising:
receiving a user's query comprising a query definition indicating a continuous query by which a single query corresponding to the user's query is continuously repeated;
receiving sensor data selected based on the query from among sensor data generated by a sensor;
analyzing the received sensor data,
wherein the receiving of the sensor data comprises:
  generating query windows, wherein each query window is a unit of a set of sensor data and the set of sensor data is used to process each query in the continuous query,
  calculating a time elapsed from a generation time of a last sensor data of each query window to a predetermined time, and
  receiving sensor data in a query window of which the calculated elapsed time is less than an allowable delay limit,
  the query further comprises the allowable delay limit indicating a maximum allowable amount of time that may elapse from a time that the sensor data is generated to a predefined time; and
the receiving of the sensor data comprises receiving sensor data used to process the user request based on whether the time elapsed from a generation time of the received sensor data to the predefined time is within the allowable delay limit.

12. The method of claim 11, wherein
the query comprises the query definition in which a user request for sensor data is defined, and
the receiving of the sensor data comprises receiving sensor data that is used to process the user request.

13. An apparatus comprising:
a user interface configured to receive a user's query comprising a query definition indicating a continuous query by which a single query corresponding to the user's query is continuously repeated;

a network interface processor configured to receive sensor data selected based on the query from among sensor data generated from a sensor; and a query processor configured to analyze the received sensor data, wherein the network interface processor is further configured to receive the sensor data based on
- generated query windows, wherein each query window is a unit of a set of sensor data and the set of sensor data is used to process each query in the continuous query,
- a calculated elapsed time from a generation time of a last sensor data of each query window to a predetermined time, and
- a query window of which the calculated elapsed time is less than an allowable delay limit;
- the first query comprises a maximum allowable amount of time that may elapse from a time that the sensor data is generated to a predefined time
- the query processor is further configured to select the sensor data based on the first query through:
- generating query windows where each query window is a basic unit of a set of sensor data that is used to process each repeated query in the continuous query,
- calculating a time elapsed from a generation time of a last sensor data of each query window to the predefined time, and
- extracting sensor data contained in at least one query window of which the calculated elapsed time is less than the allowable delay limit.

14. A non-transitory computer-readable storage medium having stored therein program instructions to cause a processor to implement a method, the method comprising:
- receiving a user's query information comprising a query definition indicating a continuous query by which a single query corresponding to the user's query is continuously repeated;
- receiving sensor data selected based on the query from among sensor data generated by a sensor; and
- analyzing the received sensor data,
- wherein the receiving of the sensor data comprises:
  - generating query windows, wherein each query window is a unit of a set of sensor data and the set of sensor data is used to process each query in the continuous query,
  - calculating a time elapsed from a generation time of a last sensor data of each query window to a predetermined time, and
  - receiving sensor data in a query window of which the calculated elapsed time is less than an allowable delay limit,
  - the first query comprises a maximum allowable amount of time that may elapse from a time that the sensor data is generated to a predefined time; and
- the receiving of the sensor data comprises receiving sensor data used to process the user request based on whether the time elapsed from a generation time of the received sensor data to the predefined time is within the allowable delay limit.

* * * * *